United States Patent [19]

Kohn et al.

[11] Patent Number: 4,806,621

[45] Date of Patent: Feb. 21, 1989

[54] BIOCOMPATIBLE, BIOERODIBLE, HYDROPHOBIC, IMPLANTABLE POLYIMINO CARBONATE ARTICLE

[75] Inventors: Joachim Kohn, Brookline; Robert S. Langer, Somerville, both of Mass.

[73] Assignee: Massachusetts Institute of Technology, Cambridge, Mass.

[21] Appl. No.: 820,351

[22] Filed: Jan. 21, 1986

[51] Int. Cl.$^4$ .............................................. C08G 63/62
[52] U.S. Cl. ..................................... 528/211; 424/78; 523/113; 523/115; 523/122; 528/128
[58] Field of Search ................... 528/211, 128; 424/78; 523/113, 115, 122

[56] References Cited

U.S. PATENT DOCUMENTS

| 3,491,060 | 1/1970 | Schminke et al. | 528/125 |
| 3,887,699 | 6/1975 | Yolles | 424/78 |
| 4,122,158 | 10/1978 | Schmitt | 424/78 |
| 4,131,648 | 12/1978 | Choi et al. | 424/78 |
| 4,419,340 | 12/1983 | Yolles | 424/78 |
| 4,554,155 | 11/1985 | Allan et al. | 424/78 |

Primary Examiner—Harold D. Anderson
Attorney, Agent, or Firm—Paul J. Cook

[57] ABSTRACT

A novel series of articles useful as medical devices, implants and protheses are provided which utilize poly(iminocarbonate) polymeric matrices. These articles are biocompatible, have excellent mechanical properties and degrade into non-toxic residues after introduction in vivo. The articles may be formed in any desired dimensions and configuration and may take specific shape as biodegradable sutures or as orthopedic appliances such as bone plates and the like.

8 Claims, 4 Drawing Sheets

BIOCOMPATIBLE, BIOERODIBLE, HYDROPHOBIC, IMPLANTABLE POLYIMINO CARBONATE ARTICLE

The Government has rights in this invention pursuant to Grant Number NIH-2-R01-GM26698-07 awarded by the National Institutes of Health.

FIELD OF THE INVENTION

The present invention is concerned with biocompatible articles suitable for surgical introduction in vivo and is particularly directed to bioerodible articles which degrade into biocompatible and non-toxic products.

BACKGROUND OF THE INVENTION

Synthetic polymeric compositions which are bioerodible and biocompatible have become increasingly important and valuable in recent years. One application for such compositions is as surgically implantable biomaterials or prosthetic articles for human and animal subjects in vivo. Consequently, such biomaterials are articles which serve as implants or prostheses, artificial devices introduced into living tissues to replace a missing part of the body; these are exemplified by articles such as vascular grafts, biodegradable sutures and orthopedic appliances such as bone plates and the like. In order for an implantable or prosthetic article to be truly useful, it should be composed of a synthetic polymeric composition having specific characteristics and properties: First, the synthetic composition should provide sufficient elasticity and tensile strength over a preselected minimal time period which will vary with the specific application. Second, the synthetic composition should be non-immunogenic, biocompatible, biodegradable in vivo and yield degradation products which are themselves non-inflammatory, non-toxic and non-antigenic.

Despite continuing research effort, very few synthetic polymeric biomaterials have been developed which provide all these desired attributes. Presently known biodegradable polymers such as polylactic acid, polyglycolic acid, polycaprolactones and the various polyamides also all lack the desired mechanical strengths over time [Heller et al, "Theory and Practice of Control Drug Delivery from Bioerodible Polymers", in *Controlled Release of Bioactive Material*, R. W. Baker Editors, Academic Press, New York, 1908, pp. 1-17; Pitt et al, *Biomaterials* 2: 215-220 (1981); Chu, C. C., *J. Appl. Polym. Sci.* 26: 1727-1734 (1981)].

Prior to this invention, polyimidocarbonates have been prepared as disclosed in U.S. Pat. No. 3,491,060. However, these polymers have not been commercially used. Specifically, they have not been considered as materials useful for implantable devices.

SUMMARY OF THE INVENTION

A bioerodible article useful for prosthesis and implantation is provided which comprises a biocompatible, polyiminocarbonate matrix, prepared in preselected dimensions and configuration, which erodes into non-toxic residues after introduction in vivo. The bioerodible article optionally can contain a pharmacologically active composition which can be released in vivo as the polyiminocarbonate article erodes in vivo. The method of using the article as an implant and prosthesis comprises the step of introducing a specifically configured article into a subject in vivo at a predetermined site.

DETAILED DESCRIPTION OF THE DRAWINGS

The present invention may be more completely and easily understood when taken in conjunction with the accompanying drawings, in which.

DETAILED DESCRIPTION OF THE PREFERRED EMBODIMENTS

The present invention comprises articles useful as implants or prostheses and methods for their preparation and use. These articles comprise a biocompatible, bioerodible, hydrophobic class of synthetic polyiminocarbonate compositions having the general formula:

$$\left[ R-O-\overset{\overset{\displaystyle NH}{\|}}{C}-O \right]_{\overline{n}}$$

wherein R contains a non-fused aromatic organic ring and n is greater than 1. This class of polymeric compositions can be formed in preselected dimensions and specific configurations. Regardless of the specific application, these compositions degrade within predictable periods of time after introduction in vivo into non-toxic, non-inflammatory and non-immunogenic residues.

The preferred embodiments of the R group within the general formulation given above is exemplified by, but is not limited or restricted to, the entities given in Table I below.

TABLE I

| R Group | |
|---|---|
| (a) |  |
| (b) |  wherein R' is lower alkyl $C_1$ to $C_6$, |
| (c) |  |

TABLE I-continued

R Group wherein n is an integer equal to or greater than 1. X is a hetero atom such as —O—, —S—, or a bridging group such as —NH—; —(S=O)—, —SO₂—, —(C=O)—, —C(CH₃)₂—, —CH(CH₃)—; —CH(CH₃)—CH₂—C(CH₃)₂—

(d)

Also compounds of the general formula below can be utilized:

wherein X is O, NH of HR''' where R''' is a low alkyl radical, R'' is a residue of a hydrocarbon including polymer such as polyolefins, an oligoglycol or polyglycol such as polyalkylene glycol ether, a polyester, polyurea, polyamine, polyurethane or polyamide.

The entire class of polyiminocarbonates can be synthesized using alternative methods of polymerization now known in the art: bulk polymerization [Conix, A., *Macro Synth.* 2: 9598 (1966)]; solution polymerization [Yoda et al, *Bull. Chem. Soc. Japan* 32: 1120-1129 (1959)]; and interfacial polymerization [Matsuda et al, Japanese Pat. No. 10,944 (1962)].

The entire class of polyiminocarbonate polymers are bioerodible and depending on the nature of the monomeric repeat unit many of them may be biocompatible. In view of their intended function as an implant or prosthesis to be introduced into a subject in vivo, it is absolutely required that these compositions be non-inflammatory, non-toxic and non-immunogenic; that is biocompatible with the subject's tissues and body fluids in all respects.

The articles comprising the present invention degrade (erode) into residues or moieties which are themselves biocompatible and non-toxic. As evidenced by the Examples which follow, each of the articles, regardless of specific polyiminocarbonate formulation used, may be implanted into the cornea of rabbits without causing inflammation even in a minor degree; this is in contrast to presently known compositions (such as polylactic acid matrices) which demonstrate at least minor inflammation of such corneal tissues. Moreover, articles comprising polyiminocarbonate compositions are demonstrably biocompatible as will be described in a study involving subcutaneous implantation of such articles in rats. Despite their presence in the living tissues over a period of weeks, no inflammatory cell infiltration (polymorphonuclear leukocytes, macrophages and lymphocytes) is seen in the tissues adjacent to the implant. Equally important, as the article predictably degrades, the degradation products are demonstrably non-mutagenic, non-cytotoxic and non-teratogenic.

It will be appreciated that these properties and characteristics, as well as the mechanical and chemical attributes, identify and distinguish such articles as being singularly suitable as implants or prostheses. The Examples which follow merely serve to illustrate one or more of the abovedescribed characteristics, which are representative of the entire class as a whole.

In one aspect of this invention, the polyiminocarbonate is mixed with a pharmacologically active composition for delivery from the implanted article. Examples of suitable biologically active substances are interferon, anti-angiogensis factors, antibodies, antigens, polysacchariads, growth factors, hormones including insulin, glucogen, parathyroid and pituitary hormones, calcitonin, vasopressin renin, prolactin, growth hormones, thyroid stimulating hormone, corticotropin, follicle stimulating hormone, luteinizing hormone and chorionic gonadotropins; enzymes including trypsin inhibitor, lysozyme, catalase, tumor angiogenesis factor, cartilage factor, transferases, hydrolases, lysases, isomerases, proteases, ligases and oxidoreductases such as esterases, phosphatases, glysidases, and peptidases; enzyme inhibitors such as leupeptin, antipain, chrymostatin and pepstatin; and drugs such as steroids, anticancer drugs or antibiotics.

The relative proportions of the composition to be released to form the two-phased system can be modified over a wide range depending upon the molecule to be administered or the desired effect. Generally, the molecule can be present in an amount which will be released over controlled periods of time, according to predetermined desired rates, which rates are dependent upon the initial concentration of the active molecule in the polymeric matrix and the rate of erosion of the polyiminocarbonate. This necessarily implies a quantity of molecules greater than the standard single dosage. Proportions suitable for the purposes of this invention can range from about 0.01 to 50 parts by weight of the active composition to between about 99.99 and about 50 parts by weight of the polymeric matrix, preferably between about 10 and about 30 parts by weight in the case of the biologically active molecule to be implanted to give 100 parts by weight of the final system.

The polymeric matrix in the composition to be released can be admixed intimately in any convenient manner, preferably by mixing the components as powders and subsequently forming the mixture into a desired shape such as by thermal forming at a temperature less than that at which the composition will become degraded and at which the polymer has desired morphological properties. Generally, the final composition is formed as a slab which can be circular, rectangular or the like and having a thickness between about 0.1 mm and about 100 mm and a total surface area between about 0.01 cm² and about 1,000 cm², preferably between about 1 cm² and about 100 cm². The delivery systems of this invention can be manufactured as devices that can take a wide range of shapes, sizes and forms by delivering the active molecule to different environments of use. For example, the systems can be made as devices including buccal and oral devices, vaginal and intrauterine devices of cylindrical, bullet, elliptical, circular, bulbous, loop, bow or any other shape that lends itself to placement in a particular environment such as an in vivo implant. The devices also include ocular devices of any geometric shape for comfortable placement in the cul de sac such as ellipsoid, bean, banana, circular, rectangular, doughnut, crescent and heart-ring shaped devices. In cross section, the ocular devices can be doubly convex, concave, concavo-convex and the like. The dimensions of the ocular devices can vary according to the size of the eye, with satisfactory eye devices generally having a length of 4-20 mm or a width of 1-15 mm and a thickness of 0.1-4 mm. Other devices made according to this invention include implants, anal, pessaries and prosthetic devices, artificial glands for dispensing a substance pharmaceutically equivalent to the corresponding neutral gland, cervical, nasal, ear and skin devices.

The polymeric matrix utilized in the present invention can be manufactured by standard techniques provided as is important to this invention that such manufacture includes process steps such as blending, mixing or the equivalent thereof for structurally defining the system comprising the molecule to be released and the polymeric matrix. For example, one suitable method for making the systems comprises the polymer and an appropriate solvent, thereby to form a casting solution, mixing a known amount of the composition to be released in the casting solution, charging the solution into a mold and then drying the mold, usually under vacuum, causing the polymer to precipitate in forming the matrix with the molecule to be released therein. Alternatively, the polymer in the form of a powder can be admixed with the molecule to be released in the form of a powder and then molded under adequate temperature and pressure to the desired shape, through injection, compression or extrusion. After the polymeric matrix containing the composition or molecule to be released is implanted in the desired aqueous environment, such as in vivo, it erodes by hydrolysis thereby releasing the composition or molecule encapsulated by the polymer.

The following examples illustrate the present invention and are not intended to limit the same.

EXAMPLE I

In this and in the following examples, all solvents were analytical grade. Hydroquinone (99% purity), potassium-t-butoxide, Bisphenol A (>99% purity) were obtained from Aldrich, triethylamine (reagent grade) from Mallinckrodt and cyanogen bromide (reagent grade) from Fisher Scientific. Poly(Bisphenol A-carbonate) [MW=32000] was obtained from Polysciences, Inc., 400 Valley Rd., Warrington, PA. Eosin Y (certification no. CE-D71) and charcoal (activated Darco G60) were purchased from MCB, Norwood, Ohio and p-nitrophenol (>99% purity) was from Fluka, Switzerland.

IR-spectroscopy was performed on a Perkin Elmer Series 1420 dispersive spectrophotometer. For transmission spectra KBr pellets were made, or thin polymer films were directly cast onto NaCl plates from diluted solutions of the polymer in methylene chloride. For "multiple internal relectance" spectra, the MIR accessory from Perkin Elmer was used, employing a KRS-5 crystal and a reflectance angle of 45°.

Thermal Analysis of polymers was done by "differential scanning caloimetry" (DSC), employing a Perkin Elmer DSC 2 Differential Scanning Calorimeter, equipped with a Perkin System 4 Thermal Analysis Microprocessor Controller and the Perkin Elmer Graphics Plotter 2. Average sample size was 10 mg and a heating rate of 20° C./min was employed.

Molecular Weight of polymers was determined by vapor pressure osmometry in a Knauer apparatus. For poly(hydroquinone-iminocarbonate), the solvent was dimethylformamide, and the measuring temperature was 90° C. For all other polymers, the measurement was performed in chloroform at 45° C.

Mechanical properties of poly(BPA-iminocarbonate) and poly(BPA-carbonate) were determined on an Instron Model 1122 stress-strain tester at an initial strain rate of 0.1 mm $mm^{-1}min^{-1}$. BPA is Bisphenol A or 2,2-bis(4-hydroxyphenyl)propane. Polymer films of 0.1 mm thickness were cast in glass dishes from methylene chloride solutions (Table 2). The films were cut into dogbone shape in accordance with ASTM-Designation D882-81 (Standard Test Methods for Tensile Properties of Thin Plastic Sheeting). Prior to testing, the polymer films were dried for 5 days in vacuum and preconditioned by storage over phosphorus pentoxide (0% humidity) at room temperature for 48 hours.

Compression Molding. Compression molded disks (diameter: 1.5 cm, thickness: 0.1 cm, weight: 250 mg) were prepared on a "Carver" laboratory press in a stainless steel mold. The appropriate quantities of powdered polymer and sieved particles (mesh 270, <53 um) of model drug were intimately mixed by grinding with a mortar and pestle. The misture was then transferred into the mold and pressed at 20,000 psi as outlined in Table 1.

Solvent Casting. Polymer solutions were prepared in methylene chloride and cast in petri dishes made of pyrex glass using the conditions summarized in Table 2. Solvent cast release devices were prepared by adding the appropriate amount of model drug to the polymer solutions. Addition of sieved Eosin Y (mesh 270, <53 um) and vortexing resulted in a uniform suspension of Eosin Y. Addition of p-nitroaniline resulted in a homogeneous solution. After casting, circular disks (diameter: 1.0 cm, thickness: 0.05-0.1 cm) were excised from the dried films with a cork borer.

Release Studies. Drug release devices were initially placed for 24 hours into 1 liter of distilled water at room temperature. All model drug released during this time was recorded as "initial burst". Thereafter, the devices were transferred into 10 ml of phosphate buffer (1.0M, pH 7.4) and kept at 37° C. Periodically the buffer was analyzed by spectroscopy (Table 3) for the amount of released model drug and/or the amount of polymer degradation products. After each such analysis the device was transferred into fresh phosphate buffer.

Synthesis

Purification of commercial hydroquinone. Commercial hydroquinone is lightly colored. The material was purified prior to use as follows: under nitrogen, 20 g hydroquinone were dissolved in 200 ml ethylacetate. The colored solution was repeatedly treated with 1 g activated carbon until a clear, colorless solution was obtained upon filtration. Colorless crystals of high purity hydroquinone were precipitated from this solution by the slow addition of 800 ml hexane. The purified material was dried in vacuum and used immediately.

Preparation of 1,4-dicyanatobenzene. The general procedure for preparation of cyanate esters was as follows: a 3-necked, 500 ml round bottom flask (equipped with thermometer, overhead stirrer and dropping funnel) was charged with a solution of 21.4 g cyanogen bromide in 100 ml absolute ether. The system was protected from moisture by a $CaCl_2$ drying tube and cooled to −10° C. by means of an external acetone-dry ice cooling mixture. 9.9 g freshly purified hydroquinone were dissolved under nitrogen in 150 ml acetone followed by the addition of 20.2 g of triethylamine. This solution was placed into the dropping funnel and kept under an atmosphere of nitrogen. With vigorous stirring, the hydroquinone/triethylamine solution was added to the cyanogen bromide solution over a period of 20 min. Temperature was kept below −5° C. (A dense, white precipitate of triethylamine hydrobromide formed). Stirring was continued for an additional 40 min.; then the reaction mixture was allowed to warm to +10° C. The precipitate was removed by filtration. The slightly colored filtrate was treated with 0.25 g activated carbon, refiltered and rapidly evaporated to dryness at a pressure of 100 mm Hg at 30° C.

Crude 1,4-dicyanatobenzene (12.1 g, 84% yield) was obtained as white crystals. The crude material was recrystallized three times from boiling carbon tetrachloride (30 g crude/l). Sometimes an insoluble oily residue remained on the bottom of the hot solution of 1,4-dicyanatobenzene in carbon tetrachloride. This residue was removed by decantation. All recrystallizations were done as quickly as possible in order to minimize exposure of the product to high temperatures. The recrystallized material consisted of fine, long, transparent needles, M.P.=117°–119° C.

Preparation of poly(hydroquinone-iminocarbonate). The procedure was as follows: 2.753 (±0.001) g of hydroquinone (freshly purified) and 4.003 (±0.001) g of 1,4-dicyanatobenzene were dissolved under nitrogen in 50 ml acetone in a sealed reaction vessel. Via a syringe, 250 ul of catalyst solution were added (catalyst solution: 56 mg/ml of potassium-t-butoxide in t-butanol). Within 1 min, the solution became noticeably viscous and within 3–5 min, a dense, white precipitate formed. After standing for 1 h at 37° C., the precipitate was extensively extracted with acetone (3 times 250 ml), collected on a Buchner funnel and dried to constant weight in vacuo. Poly(hydroquinone-iminocarbonate) was obtained as a soft powder (6.2 g, 92% yield).

Preparation of BPA-dicyanate (2,2-di-(4'-cyanatophenyl)propane). BPA-dicyanate was prepared in the same way as 1,4-dicyanate (see above) with the following modifications: 21.4 g cyanogen bromide were dissolved in 100 ml acetone and placed into the three-necked flask. 20.5 g of BPA and 20.2 g of triethylamine were dissolved in 150 ml acetone and placed in the dropping funnel. No efforts were made to exclude oxygen. After completion of the reaction, the dense precipitate of triethylamine hydrobromide was removed by Buchner filtration. To the clear, colorless filtrate, 500 ml of ice-cold water was added slowly and with stirring over the course of 5 min. A dense, crystalline precipitate of crude BPA-dicyanate formed, which was collected on a Buchner funnel, washed with ice-cold water and rapidly dried over phosphorous pentoxide in vacuum. Crude BPA-dicyanate was obtained as a white crystalline solid (21.5 g, 86% yield). The crude material was recrystallized three times from hexane (16 g crude/l) in the same way as 1,4-dicyanatobenzene (see above). The recrystallized material consisted of long needles, M.P.=82°–83° C.

Preparation of poly(BPA-iminocarbonate). 5.7534 (±0.001) g BPA and 7.0137 (±0.001) g BPA-dicyanate were dissolved at room temperature in 15 ml acetone. With stirring, 250 ul catalyst solution was added (catalyst solution: 56 mg/ml of potassium-t-butoxide in t-butanol). Within 5 min, the reaction vessel warmed up noticeably and the solution became viscous. After about 15 min, the reaction mixture completely solidified. It was kept at 37° C. for 2 h, after which the polymer was extracted 3 times with 250 ml acetone and dried in vacuo. Crude poly(BPA-iminocarbonate) was obtained as a tough, transparent solid (12.6 g, 98% yield).

EXAMPLE II

Toxicological Screening of poly(BPA-iminocarbonate)

Preparation of the polymer for toxicological testing was done as follows: a 10% (w/w) solution of crude poly(BPA-imincarbonate) in methylene chloride was filtered and slowly added into a 20 fold excess of isopropanol. Poly(BPA-iminocarbonate) precipitated in large lumps. The precipitated material was collected under sterile conditions and dried in high vacuum to constant weight.

Rabbit eye tests were performed as described in Langer et al, J. Biomed. Mat. Res. 15: 267–277 (1981) using solvent cast films (approximate size: 0.1 cm*0.1 cm*0.05 cm) of poly(BPA-iminocarbonate), which were implanted into the corneas of male New Zealand White Rabbits.

For subcutaneous implantation circular disks (diameter: 0.3 cm, thickness: 0.05 cm, weight: 2.5 mg) were cut from solvent cast films of purified poly(BPA-iminocarbonate). The disks were sterilized by short immersion in 70% aqueous isopropanol and implanted subcutaneously in the back of male CD-1 mice (CRBL-Kingston). At specific intervals animals were sacrificed, the residual polymer retrieved, the implantation site was inspected for any pathological changes and the histology of tissues surrounding the implant was examined.

EXAMPLE III

As a starting point for the investigations, we chose poly(hydroquinone-iminocarbonate) as a model system. The IR-spectrum of this material showed absorption bands, which can be assigned to the iminocarbonate bond, in addition to absorptions which corresponded to free cyanate ester and hydroxyl terminal groups.

Figure 1:
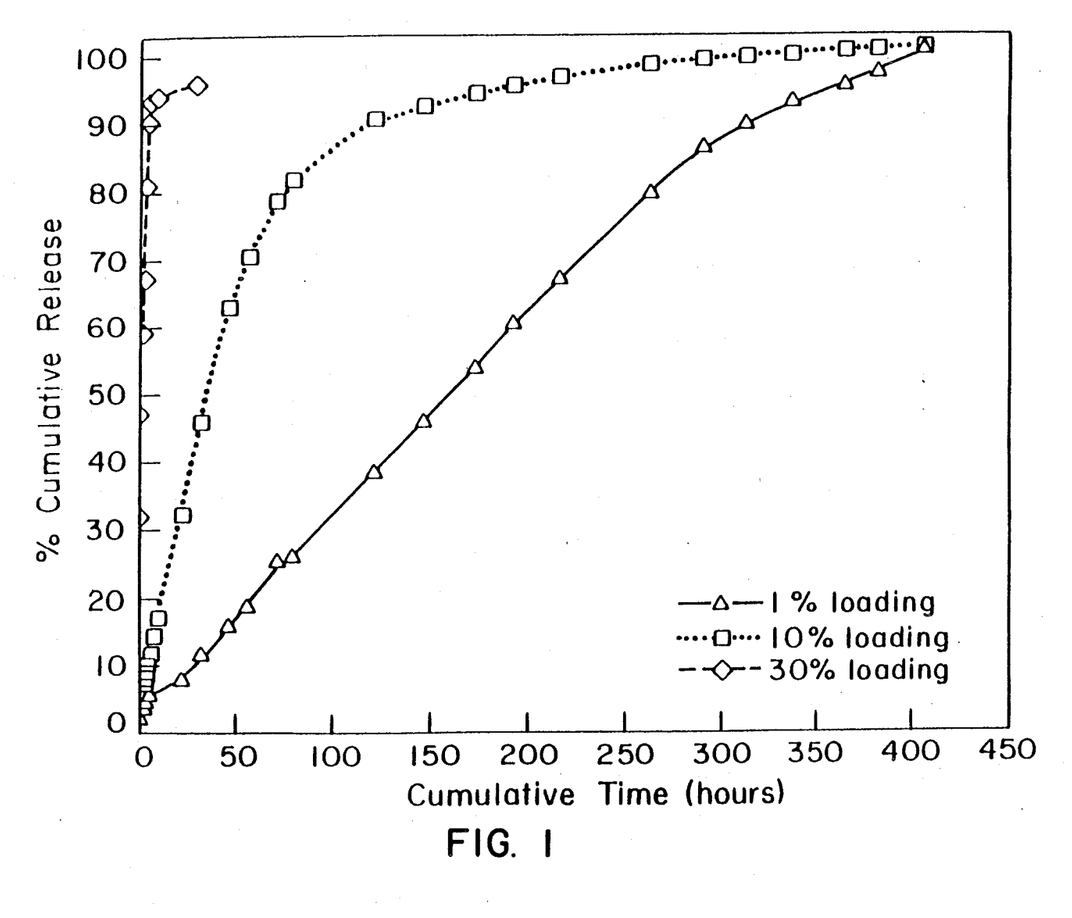
FIG. 1 shows the rate of release of Eosin Y from compression molded disks of poly(hydroquinone-iminocarbonate) at 37° C. in 0.1M phosphate buffer (pH 7.4). Eosin Y loadings were 1%, 10% and 30% (w/w) as indicated.

A number of properties of poly(hydroquinone-iminocarbonate) are summarized in Table 4. Due to its insolubility in all tested volatile solvents, poly(hydroquinone-iminocarbonate) could not be solvent cast). Likewise its marked thermal degradation in the molten state precluded high temperature fabrication methods such as injection molding. However, compression molding proved satisfactory and opaque, slightly brittle disks could be prepared. By blending the sieved polymer powder with up to 30% (w/w) of Eosin Y (which served as model compound for hydrophilic, low molecular weight drugs), Eosin Y containing disks were prepared. The release characteristics of these disks (FIG. 1) were strongly dependent on the loading: at a loading of 30% (w/w), the device started to crumble within 3 h and Eosin Y was released rapidly and without correlation to polymer erosion. At low loadings (1%), Eosin Y was released over 400 h at a rate which remained nearly constant with time throughout the entire release process. This result suggests that Eosin Y release is not due to a simple diffusional mechanism.

Next poly(BPA-iminocarbonate) was investigated. Some physical and chemical properties of poly(BPA-iminocarbonate) are summarized in Table 4. Contrary to poly(hydroquinone-iminocarbonate), poly(BPA-iminocarbonate) is soluble in many organic solvents. Poly(BPA-iminocarbonate) could be solvent cast, yielding clear, transparent films. From concentrated solutions in methylene chloride (30% w/w) fibers could be drawn. The molecular structure of poly(BPA-iminocarbonate) was confirmed by elemental analysis and IR-spectroscopy. The IR-spectrum of a thin film of poly(B-

PA-iminocarbonate) is similar to the spectrum of commercially available poly(BPA-carbonate) except for iminocarbonate absorption at 3340 cm$^{-1}$ (N—H) and 1680 cm$^{-1}$ (C=N).

The stress-strain behavior of poly(BPA-iminocarbonate) was investigated and compared to the behavior of a low molecular weight commercial sample of poly(BPA-carbonate) (MW=32000). Since the stress-strain behavior of polymers depends to a large extent on the way the samples are prepared, cut and preconditioned prior to measurement, care was taken to prepare samples of both polymers in an identical fashion and to test them under the same conditions. The results of these experiments are summarized in Table 5. These data indicate that poly(BPA-iminocarbonate) is a tough, strong polymer with exceptionally high tensile strength. As a general rule, both toughness and tensile strength increase with increasing molecular weight. Therefore, it is encouraging that poly(BPA-iminocarbonate) with a molecular weight of only 12,000 would have mechanical properties which compare favorably to those of commercial poly(BPA-carbonate) resins of much higher molecular weight. In this context, it is interesting to note that for poly(lactic acid) MW=13,000) a tensile strength of 3200 psi has been reported. Although not directly comparable to the measured value, it seems that poly(BPA-iminocarbonate) has a higher tensile strength than poly(lactic acid), which is widely used as biodegradable suture.

Monomeric iminocarbonates were previously shown to have two different degradation pathways, depending on the pH of the surrounding medium. However, no information was available pertaining to the mode of hydrolysis of poly(iminocarbonates) at neutral pH. Therefore, an initial study of the hydrolysis of poly(BPA-iminocarbonate) was performed, employing "Multiple Internal Reflectance"-IR-spectroscopy (MIR-IR). Freshly cast films of poly(BPA-iminocarbonates) had MIR-spectra indistinguishable from regular transmission IR-spectra. However, after exposure of these films for only 60 min to 0.1M phosphate buffer (pH 7.4) at 70° C., a strong band at 1770 cm$^{-1}$ appeared. This absorption band is characteristic for carbonates and provides evidence for the formation of carbonate bonds during the degradation of poly(BPA-iminocarbonate) at neutral pH.

In order to obtain quantitative data on the extent of carbonate formation during hydrolysis, an accelerated degradation study was performed at 70° C. Films of poly(BPA-imincarbonate) (dimensions: 2 cm×1 cm×0.1 cm) were extensively hydolized in either 0.1N hydrochloric acid (pH 1), 0.1M phosphate buffer (pH 7.4) or 0.1N sodium hydroxide (pH 14) as hydrolysis medium. During the course of hydrolysis, the amount of BPA accumulating in the release medium was monitored by UV spectroscopy.

The most rapid hydrolysis was observed in sodium hydroxide: films of poly(BPA-iminocarbonate) dissolved completely within 5 days. 96% of the theoretical amount of BPA could be recovered in the hydrolysis medium. The films became noticeably thinner while maintaining their structural integrity up to the very last stage of degradation. This behavior seemed to indicate "surface erosion". However, since erosion in hot 0.1N NaOH is of no practical interest, this phenomenon was not further investigated. The mechanism of hydrolysis was different in hydrochloric acid and in phosphate buffer (pH 7.4). In those media, the initially transparent films became opaque within 24 h and started to crumble within 2 days. By day 3, only white, flaky precipitates were left. Surprisingly, at this point only about 7–14% of the theoretical amount of BPA could be recovered from the hydrolysis medium. The release of BPA continued slowly for about 25 days, finally leveling off at a total accumulated recovery of 51% (in HCl) and 72% (in phosphate buffer) of the theoretical amount of BPA. At this point, the white, flaky residues were collected, dried, weighed and analyzed by IR spectroscopy (KBr-pellet). Their IR spectra closely resembled the spectrum of poly(BPA-carbonate). By vapor pressure osmomtry the molecular weight of these residues was found to be 475(±100), suggesting that they consisted mostly of dimers or trimers of BPA-carbonate. The results of this study are summarized in Table 6.

These observations suggest that at neutral pH, poly(BPA-iminocarbonate) hydrolyzes by a combination of two different pathways: Backbone cleavage and release of BPA occurs concomitantly to the formation of the more stable carbonate bond. This process results in the formation of the observed white, flaky precipitates. Since carbonate formation is catalyzed by acid, the extent of carbonate formation should increase as the acidity of the hydrolysis medium increases. This expectation was confirmed by experimental results: The overall proportion of carbonate formation was higher in HCl (45%) than in phosphate buffer (28%), (Table 6).

In order to obtain an estimate for the rate of hydrolysis at 37° C., the hydrolysis experiments were repeated at that temperature: the hydrolysis of poly(BPA-iminocarbonate) showed the same general pattern as at 70° C. (Table 6), but was markedly slower: for instance, in phosphate buffer (physiological conditions), a solvent cast film (dimensions: 2 cm×1 cm×0.1 cm) of poly(BPA-iminocarbonate) became opaque by day 40 (no BPA released), holes and cracks were visible by day 61 (5 mol% BPA released), the polymer crumbled on day 109 (11 mol% BPA released) and by day 200, only flaky precipitates of BPA-carbonate were lest (35 mol% BPA released).

Figure 2:
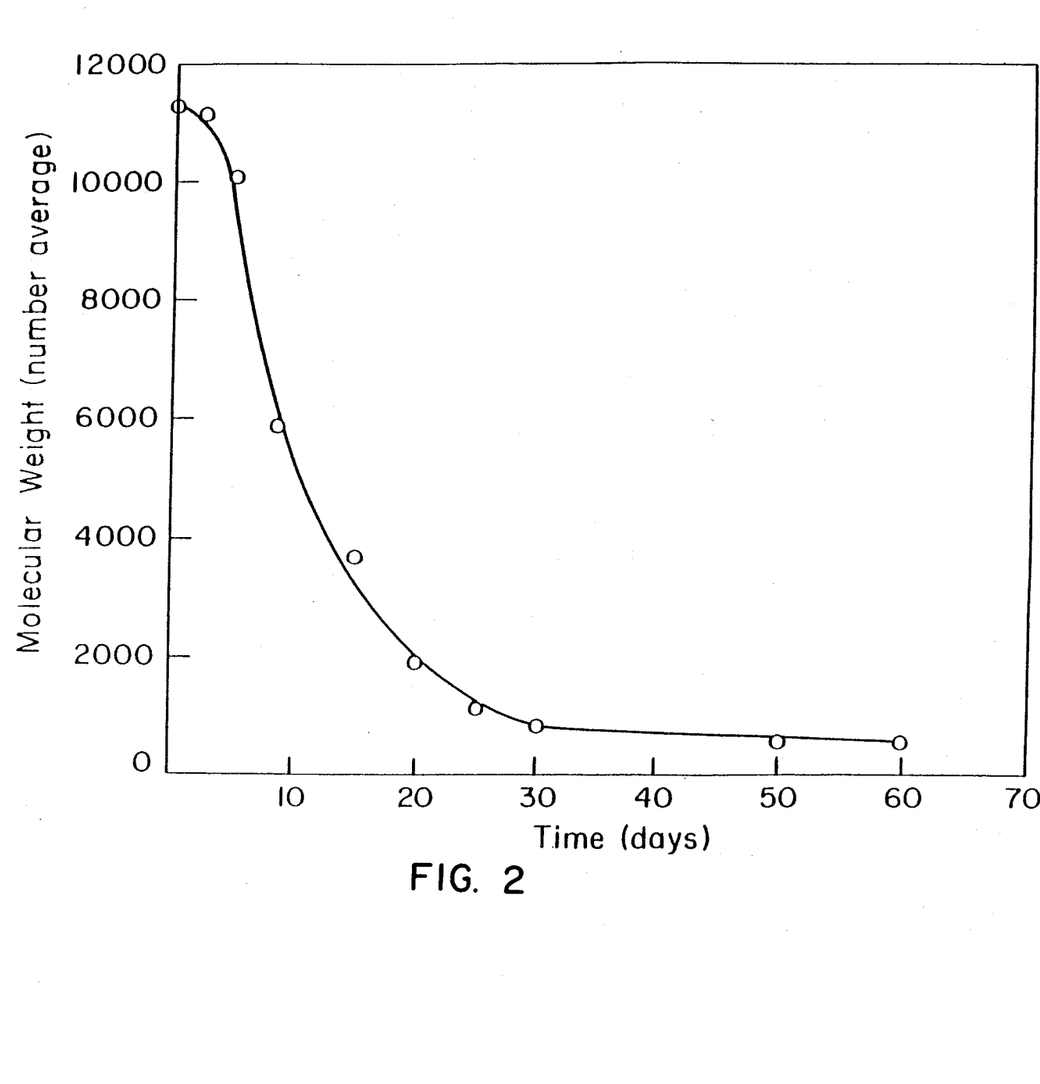
FIG. 2 shows the decrease of molecular weight (number average) during hydrolysis (in 0.1M phosphate buffer, pH 7.4, 37° C.) of thin films of poly(Bisphenol A-iminocarbonate).

In a parallel experiment, the changes in the molecular weight (number average) of solvent cast films (dimensions: 2 cm×1 cm×0.1 cm) of poly(BPA-iminocarbonate) were followed during hydrolysis under physiological conditions. After various hydrolysis times, samples of film were removed, dried, weighed and their residual molecular weight determined by vapor pressure osmometry. As shown in FIG. 7, the molecular weight decreased rapidly, indicating that extensive backbone cleavage occurred within 30 days of exposure to buffer. During this period, the films became opaque and brittle and lost 99% of their initial tensile strength. However, no weight loss occurred—in correspondence to our observation that no BPA is released from the films during this initial stage of the hydrolysis.

Figure 3:
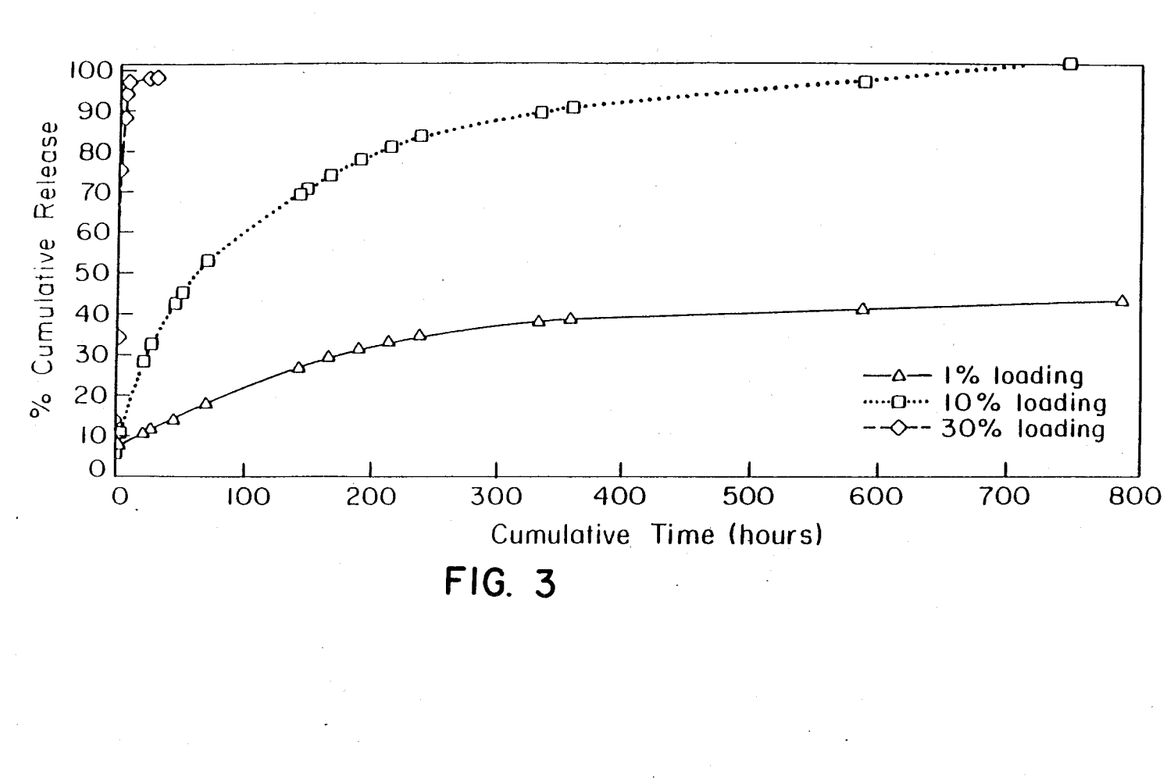
FIG. 3 shows the release of Eosin Y from compression molded disks of poly(Bisphenol A-iminocarbonate) at 37° C. in 0.1M phosphate buffer, pH 7.4. Eosin Y loadings were 1%, 10% and 30% (w/w) as indicated.
Figure 4:
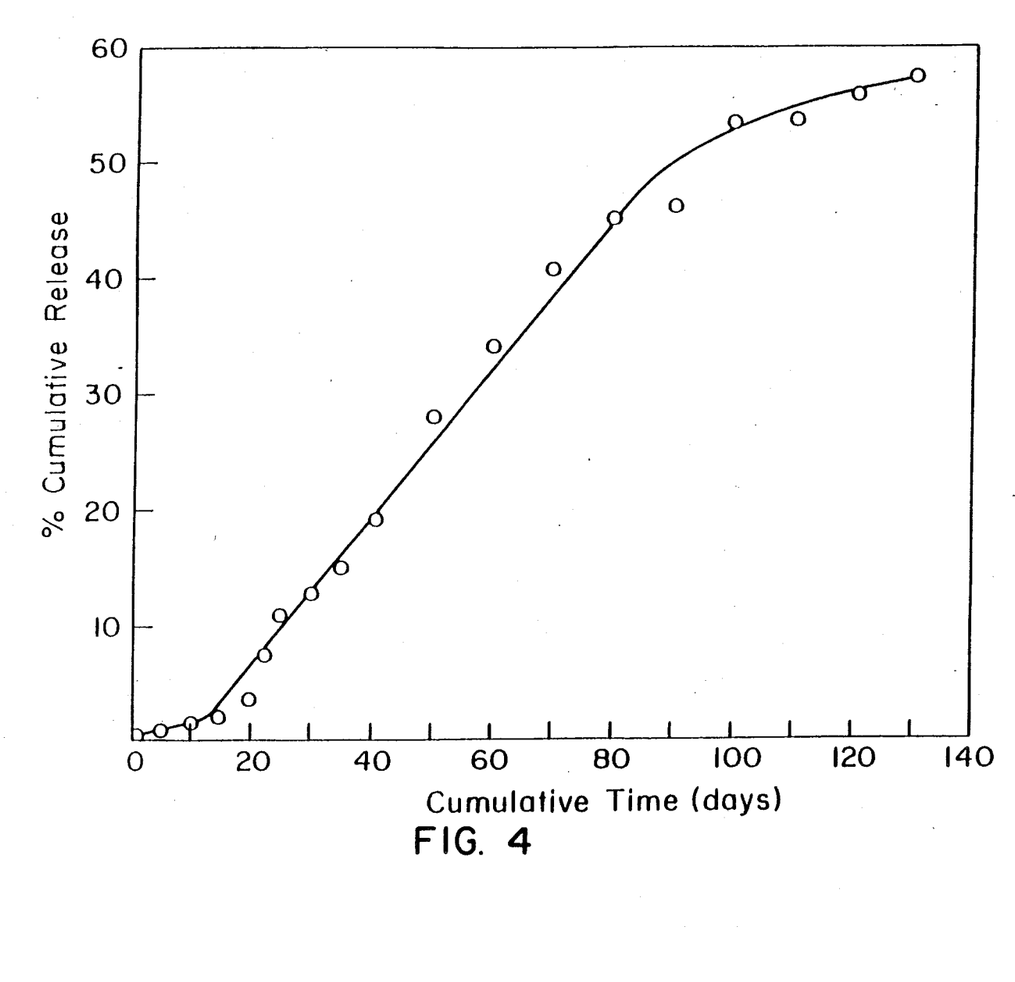
FIG. 4 shows the release of p-nitroaniline from solvent cast films of poly(Bisphenol A-iminocarbonate) at 37° C. in 0.1M phosphate buffer, pH 7.4. p-Nitroaniline loading was 10% (w/w).

The use of poly(BPA-iminocarbonate) for drug delivery applications was investigated using p-nitroaniline and Eosin Y as model compounds for low molecular weight, hydrophobic and hydrophilic drugs respectively. In order to compare poly(BPA-iminocarbonate) to poly(hydroquinone-iminocarbonate), compression molded disks of poly(BPA-iminocarbonate) were prepared, containing loadings of 1%, 10% or 30% (w/w) of Eosin Y. These devices were prepared in the same manner as those made of poly(hydroquinone-iminocarbonate). The release profiles (FIG. 3) were dependent on the degree of loading: at high loading (30% w/w), all Eosin Y was released within 8 h, whereas at low loadings (1% and 10% w/w), more sustained release was obtained. As compared to poly(hydroquinone-iminocarbonate), release from poly(BPA-iminocarbonate) was significantly prolonged at the 1% and 10% loading level. Solvent cast films of poly(BPA-iminocarbonate) containing 10% (w/w) of Eosin Y were also tested. Since Eosin Y is insoluble in methylene chloride, these films were heterogeneous two-phase systems consisting of sieved Eosin Y particles (mesh 270, <53 um) dispersed within the polymeric phase. Surprisingly, no Eosin Y could be released from these films beyond a short, initial burst during the first 24 h. In order to study the behavior of more hydrophobic model drugs, solvent cast films were prepared containing 10% (w/w) of p-nitroaniline. Since p-nitroaniline is soluble in methylene chloride, the resulting films were homogeneous. These films were transparent, clear and pliable. The release profile of p-nitroaniline (FIG. 4) is characterized by a lag period of about 15 days. Thereafter, a prolonged period of zero-order release was observed (90 days), which is desirable for many controlled release applications.

For the assessment of the possible toxicity of poly(BPA-iminocarbonate), the individual toxicities of the monomers (BPA and BPA-dicyanate) must be considered in addition to the individual toxicities of the known degradation products (carbon dioxide, ammonia, poly(BPA-carbonate) and BPA).

Poly(BPA-carbonate) has been studied extensively and is regarded as a non-toxic, biocompatible polymer. Large subcutaneous implants (25 g/kg) in rats had no toxic effect. BPA was also extensively investigated; the $LD_{50}$ for oral administration is well above 2 g/kg in all tested species. Furthermore, continuous exposure of mice to a total dose of 865 g/kg over a period of 2 years (equivalent to approximately 1.18 g/kg per day) failed to show carcinogenicity (NCI bioassay). For comparison, use of a polymeric drug delivery system with a volume of about 1 $cm^3$ could expose the patient to about 1 g of BPA over a period of 200 days resulting in an average daily exposure of about 0.00007 g/kg.

The cyanate function (OCN) seems to be devoid of the acute toxicity associated with derivatives of cyanide ($CN^-$). For example, sodium or potassium cyanate (KOCN) are only moderately toxic ($LD_{50}$ for potassium cyanate, i.p. (mouse)=320 mg/kg). Sodium cyanate has been used as an experimental drug in humans for treatment of sickle-cell anemia and estrogen cyanate was administered to women as a contraceptive agent. In general, the non-volatile cyanates have no irritating effect on skin or mucous membranes and very low systemic toxicity in humans. In particular, BPA-dicyanate was extensively tested. These studies (Table 7) indicate that the cyanate function in BPA-dicyanate does not increase the acute toxicity of this compound as compared to BPa itself. Likewise, chronic respiratory exposure of guinea pigs, mice and rats to BPA-dicyanate at a concentration of 400 mg/$m^3$ (4 hours per day for a total of 4 weeks) did not produce any symptoms of toxicity and no changes in blood chemistry and kidney or liver function were noted.

Based on these data, neither the monomers nor the known degradation products of poly(BPA-iminocarbonate) were sufficiently toxic to preclude—a priori— —the possible use of poly(BPA-iminocarbonate) in medical applications. Therefore, in vivo tests of the tissue compatibility of poly(BPA-iminocarbonate) were performed. In the rabbit cornea test, no signs of inflammation (4 animals) were detected over a period of 4 months post-implantation. In a second test, poly(BPA-iminocarbonate) was implanted subcutaneously into male CD-1 mice (10 animals). These animals were sacrificed at times ranging from 8 to 24 weeks post-implantation. Gross postmortem observation revealed no inflammation or other lesions at the implantation site in any of the animals. Histological examination showed a very thin layer of connective tissue around the implant; however, there was a complete lack of inflammatory cells (e.g., polymorphonuclear leukocytes, macrophages) at the implantation site. While the above tests do not constitute a complete toxicological assessment, they suggest that poly(BPA-iminocarbonate) implants have a high degree of tissue-compatibility.

TABLE 1

| | Conditions for Compression Molding | |
|---|---|---|
| Polymer | Temperature (°C.) | Time (min) |
| poly(hydroquinone-iminocarbonate) | 70 | 10 |
| poly(BPA-iminocarbonate) | 100 | 20 |
| poly(BPA-carbonate) | 150 | 30 |

TABLE 2

| | Conditions for Solvent Casting | |
|---|---|---|
| Polymer | Concentration of Casting Solution in % (w/w) | Casting Temperature (°C.) |
| poly(BPA-carbonate) | 10 | 37 |
| poly(BPA-iminocarbonate) | 20 | 25 |

TABLE 3

| Spectroscopic Determination of Model Drugs and BPA | | |
|---|---|---|
| Compound | Peak Wavelength (nm) | Extinction Coefficient (liter $mol^{-1}$ $cm^{-1}$) |
| Eosin Y | 518 | 79400 |
| p-nitroaniline | 403 | 12900 |
| BPA | 244 | 18700 |

TABLE 4

| Some Physical Properties of Poly(iminocarbonates) | | |
|---|---|---|
| Property | Poly(hydroquinone-iminocarbonate) | Poly(BPA-iminocarbonate) |
| appearance | white powder | tough, transparent solid |
| glass transition temperature (Tg) | 61° C. | 75° C. |
| melting range | decomposes before melting | decomposes before melting |
| molecular weight (number average) | 2000 | 12000 |
| thermal stability | degrades above 130° C. | degrades above 160° C. |
| solubility | soluble in: dimethylsulfoxide, dimethylformamide insoluble in: water, alcohol, acetone, ether, benzene, chlorinated hydrocarbons, hexane | soluble in: chlorinated, hydrocarbons, dimethylformamide, dimethylsulfoxide partially soluble in: acetone, benzene insoluble in: water, alcohol, ether, hexane |

TABLE 5

| | Poly(BPA-iminocarbonate)[a] | Poly(BPA-carbonate) | |
|---|---|---|---|
| Property | (MW = 12000) | MW = 32000[a] | MW = 70–80000[b] |
| modulus of elasticity | 112000 psi | 134000 psi | 320000 psi |
| yield stress | 7000 psi | 5780 psi | — |
| tensile strength (nominal) | 7530 psi | 6910 psi | 10500 psi |
| elongation at break | 38% | 109% | 60–100% |
| tensile energy to break | 16 * 10⁶ J/m³ | 34 * 10⁶ J/m³ | — |

Mechanical Properties of Poly(BPA-iminocarbonate)

[a] solvent cast films, prepared and tested as described in Materials and Methods
[b] literature values (12, 13) reported for commercial grade resins, having a molecular weight of about 70000–80000

TABLE 6

Hydrolysis of Poly(BPA-iminocarbonate)

| Hydrolysis Temperature (°C.) | Hydrolysis Medium | BPA Recovered (mol %) | Carbonate Recovered (mol %) | Complete Hydrolysis (days) |
|---|---|---|---|---|
| 37 | 0.1 N NaOH | >90 | 0 | 82 |
| | 0.1 N HCl | 20 | 72 | 200 |
| | phosphate (pH 7.4) | 35 | 63 | >200 |
| 70 | 0.1 N NaOH | >96 | 0 | 5 |
| | 0.1 N HCl | 51 | 45 | 18 |
| | phosphate (pH 7.4) | 72 | 28 | 32 |

TABLE 7

Toxicity of BPA-dicyanate[a]

| Mode of Administration | LD$_{50}$ (Rat) |
|---|---|
| oral | >2500 mg/kg |
| subcutaneous | >2500 mg/kg |
| inhalation[b] | >440 mg/m³ |

[a] according to data of Farbenwerke Bayer, Wuppertal-Elberfeld, W. Germany
[b] particles in air

We claim:

1. An article useful for implantation in an animal comprising a mixture of (a) a solid biocompatible, bioerodible, hydrophobic polyiminocarbonate composition having the recurring structrual unit:

wherein R is a divalent aromatic group comprising a non-fused ring and n is at least 2, said article degrading into non-toxic residues after introduction in vivo and (b) a pharmacologically active composition.

2. The article recited in claim 1 wherein R is phenylene.

3. The article recited in claim 1 wherein R is:

4. The article as recited in claim 1 wherein R is:

5. The article as recited in claim 1 wherein R is:

and R' is C,-C$_6$ lower alkylene.

6. The article of claim 1 wherein R is:

X is a heteroatom and n is an integer greater than 1.

7. The article of claim 1 wherein R is:

8. The process for administering a pharmacologically active composition to an animal which comprises implanting in said animal the article of any one of claims 2, 3, 4, 5, 6, 7 or 1.